(12) United States Patent
Kuvettu et al.

(10) Patent No.: US 10,894,248 B2
(45) Date of Patent: Jan. 19, 2021

(54) CATALYST COMPOSITION FOR ENHANCING YIELD OF OLEFINS IN FLUID CATALYTIC CRACKING PROCESS (FCC)

(71) Applicant: INDIAN OIL CORPORATION LIMITED, Mumbai (IN)

(72) Inventors: Mohan Prabhu Kuvettu, Faridabad (IN); Arumugam Velayutham Karthikeyani, Faridabad (IN); Velusamy Chidambaram, Faridabad (IN); Kumaresan Loganathan, Faridabad (IN); Alex Cheru Pulikottil, Faridabad (IN); Sanjiv Kumar Mazumdar, Faridabad (IN); Sankara Sri Venkata Ramakumar, Faridabad (IN)

(73) Assignee: INDIAN OIL CORPORATION LIMITED, Mumbai (IN)

(*) Notice: Subject to any disclaimer, the term of this patent is extended or adjusted under 35 U.S.C. 154(b) by 0 days.

(21) Appl. No.: 16/528,477

(22) Filed: Jul. 31, 2019

(65) Prior Publication Data

US 2020/0086304 A1 Mar. 19, 2020

(30) Foreign Application Priority Data

Sep. 13, 2018 (IN) .............................. 201821034591

(51) Int. Cl.
*B01J 29/06* (2006.01)
*B01J 29/80* (2006.01)
*C10G 11/05* (2006.01)
*B01J 29/08* (2006.01)
*B01J 29/40* (2006.01)
*B01J 21/16* (2006.01)

(Continued)

(52) U.S. Cl.
CPC ............... *B01J 29/80* (2013.01); *B01J 21/12* (2013.01); *B01J 21/16* (2013.01); *B01J 23/002* (2013.01); *B01J 23/005* (2013.01); *B01J 23/72* (2013.01); *B01J 27/16* (2013.01); *B01J 29/08* (2013.01); *B01J 29/088* (2013.01); *B01J 29/126* (2013.01); *B01J 29/146* (2013.01); *B01J 29/16* (2013.01); *B01J 29/166* (2013.01); *B01J 29/40* (2013.01); *B01J 29/46* (2013.01); *B01J 29/48* (2013.01); *B01J 29/7415* (2013.01); *B01J 29/7615* (2013.01); *B01J 35/026* (2013.01); *B01J 35/08* (2013.01); *B01J 37/0018* (2013.01); *B01J 37/0045* (2013.01); *B01J 37/0072* (2013.01); *B01J 37/04* (2013.01); *B01J 37/08* (2013.01); *B01J 37/28* (2013.01); *C07C 4/00* (2013.01); *C10G 11/05* (2013.01); *B01J 2029/062* (2013.01); *B01J 2229/186* (2013.01); *B01J 2229/20* (2013.01); *C07C 2521/04* (2013.01); *C07C 2521/08* (2013.01); *C07C 2521/12* (2013.01); *C07C 2521/16* (2013.01); *C07C 2523/72* (2013.01); *C07C 2529/10* (2013.01); *C07C 2529/12* (2013.01); *C07C 2529/14* (2013.01); *C07C 2529/16* (2013.01); *C07C 2529/20* (2013.01); *C07C 2529/22* (2013.01); *C07C 2529/24* (2013.01); *C07C 2529/26* (2013.01); *C07C 2529/42* (2013.01); *C07C 2529/44* (2013.01); *C07C 2529/46* (2013.01); *C07C 2529/48* (2013.01); *C07C 2529/74* (2013.01); *C07C 2529/76* (2013.01); *C07C 2529/78* (2013.01); *C07C 2529/80* (2013.01); *C10G 2300/70* (2013.01); *C10G 2400/02* (2013.01); *C10G 2400/04* (2013.01); *C10G 2400/20* (2013.01)

(58) Field of Classification Search
CPC ........ B01J 29/126; B01J 29/146; B01J 29/16; B01J 29/166; B01J 29/088; B01J 29/08; B01J 29/80; B01J 29/40; B01J 29/46; B01J 29/48; B01J 29/7415; B01J 29/7615; B01J 2229/20; B01J 2229/42; B01J 2229/186; B01J 23/002; B01J 23/005; B01J 35/026; B01J 35/08; B01J 27/16; B01J 21/16; B01J 21/12; B01J 37/008; B01J 37/0018; B01J 37/04; B01J 37/0045; B01J 37/0072; B01J 37/28; B01J 2029/062; C07C 2521/04; C07C 2521/08; C07C 2521/12; C07C 2521/16; C07C 2529/10; C07C 2529/12; C07C 2529/14; C07C 2529/16; C07C 2529/20; C07C 2529/22; C07C 2529/24; C07C 2529/26; C07C 2529/42; C07C 2529/44; C07C 2529/46; C07C 2529/48; C07C 2529/74; C07C 2529/76; C07C 2529/78; C07C 2529/80
USPC ................ 502/63, 64, 65, 66, 67, 68, 69, 71
See application file for complete search history.

(56) References Cited

U.S. PATENT DOCUMENTS 3,541,179 A 11/1970 Okagami et al.
3,647,682 A 3/1972 Rabo et al.
(Continued)

FOREIGN PATENT DOCUMENTS

DE 152356 A1 11/1981
EP 0490886 A2 6/1992
WO WO 97/12011 * 4/1997

*Primary Examiner* — Elizabeth D Wood
(74) *Attorney, Agent, or Firm* — Maschoff Brennan

(57) ABSTRACT

The present invention provides a catalyst composition comprising rare earth exchanged USY zeolite (REUSY); pentasil zeolite; phosphorous compound; clay, silica, alumina, and spinel to enhance the catalytic activity and selectivity for light olefins in FCC operation conditions. The present invention also provides a process for the preparation of Light olefin enhancing catalyst composition with high propylene yield and coke selectivity.

10 Claims, No Drawings

(51) Int. Cl.
- *B01J 21/12* (2006.01)
- *B01J 23/00* (2006.01)
- *B01J 23/72* (2006.01)
- *B01J 27/16* (2006.01)
- *B01J 35/02* (2006.01)
- *B01J 35/08* (2006.01)
- *B01J 37/04* (2006.01)
- *B01J 37/00* (2006.01)
- *B01J 37/08* (2006.01)
- *C07C 4/00* (2006.01)
- *B01J 29/48* (2006.01)
- *B01J 29/12* (2006.01)
- *B01J 29/46* (2006.01)
- *B01J 29/14* (2006.01)
- *B01J 29/16* (2006.01)
- *B01J 29/76* (2006.01)
- *B01J 29/74* (2006.01)
- *B01J 37/28* (2006.01)

(56) References Cited

U.S. PATENT DOCUMENTS

| | | | |
|---|---|---|---|
| 4,493,902 A * | 1/1985 | Brown | B01J 29/084 423/712 |
| 4,980,053 A | 12/1990 | Li et al. | |
| 5,055,176 A | 10/1991 | Herbst et al. | |
| 5,318,696 A | 6/1994 | Kowalski | |
| 5,326,465 A | 7/1994 | Yongqing et al. | |
| 5,380,690 A | 1/1995 | Zhicheng et al. | |
| 5,389,232 A | 2/1995 | Adewuyi et al. | |
| 5,846,402 A | 12/1998 | Mandal et al. | |
| 6,528,447 B1 | 3/2003 | Ghosh et al. | |
| 6,716,338 B2 * | 4/2004 | Madon | B01J 29/084 208/118 |
| 6,905,591 B2 | 6/2005 | Letzsch et al. | |
| 7,375,256 B2 | 5/2008 | Xie et al. | |
| 9,616,408 B2 | 4/2017 | Karthikeyani et al. | |
| 9,796,932 B2 * | 10/2017 | Smith | C10G 11/04 |
| 2009/0149317 A1 * | 6/2009 | Stamires | B01J 37/031 502/63 |
| 2013/0066131 A1 * | 3/2013 | Harris | C07C 4/06 585/653 |
| 2013/0317271 A1 * | 11/2013 | Al-Ghrami | B01J 38/02 585/653 |
| 2015/0174559 A1 * | 6/2015 | Smith | B01J 21/04 208/114 |
| 2015/0175899 A1 * | 6/2015 | McGuire, Jr. | B01J 21/02 208/114 |
| 2015/0352541 A1 * | 12/2015 | Stamires | B01J 29/7007 252/183.13 |
| 2016/0074842 A1 | 3/2016 | Sarkar et al. | |
| 2017/0144137 A1 * | 5/2017 | Smith | B01J 21/16 |

* cited by examiner

CATALYST COMPOSITION FOR ENHANCING YIELD OF OLEFINS IN FLUID CATALYTIC CRACKING PROCESS (FCC)

FIELD OF THE INVENTION

The present invention relates to a Fluid Catalytic Cracking (FCC) catalyst composition for upgrading low value, high boiling hydrocarbon feed stock. More specifically, the present invention relates to the FCC catalysts and the process for preparation thereof wherein the FCC catalyst composition offers dual functions of simultaneous enhancement of $C_3$ to $C_4$ olefins and arresting the loss of distillates in slabs of gasoline, heavy naphtha, and light cycle oil while processing low value and high boiling feeds.

BACKGROUND OF THE INVENTION

Motor fuels such as gasoline and diesel are essential and it is considered to be the major products of conventional fluid catalytic cracking (FCC) process. The reported yield of light olefins production is limited to 15 wt % and LPG is limited to 10 to 25 wt % employing variety of feedstock in a boiling range of 370 to 500° C. Light olefin and LPG products are considered as by-products in conventional FCC process. There have been continuous studies and various investigations for converting petroleum hydrocarbons to gaseous olefins as major product in FCC process suitable for petrochemical feedstock.

U.S. Pat. No. 3,541,179 discloses FCC process for producing gaseous olefins employing metal supported silica and alumina catalyst. Another U.S. Pat. No. 3,647,682 describes the production of olefins from butane/distillate feed over Y-zeolites. FCC process developed by employing amorphous silica-alumina catalyst is described in DD. No 152, 356 to convert vacuum gas oil to $C_2$ to $C_4$ olefin at the temperature of 600 to 800° C., which yields 13.5% of ethylene, 6.3% for propylene and 10.5% of butylenes.

Yet another process is disclosed in JP No 60-222,428 for the production of 30% of $C_2$ to $C_4$ olefins at temperature of 600 to 750° C. using ZSM-5 as a catalyst. The patent discloses that ethylene (16%), propylene (14%) and butylenes (1.8%) were obtained when naphtha is used as feed. EP0490886 discloses the process for the production of Olefin and aromatics from hydrocarbon feed stock by catalytic cracking.

U.S. Pat. No. 5,389,232 discloses riser cracking process utilizing 3 wt % of ZSM-5 additive along with FCC catalyst which results in the $C_3/C_4$ olefin of 7 wt % and LPG of 18 wt %. Another U.S. Pat. No. 5,055,176 discloses catalyst composition comprising of Y-zeolite, Ga-ZSM-5 and alumina matrix to produce olefin, such as propylene and ethylene at 8-10 wt % employing VGO as feed.

U.S. Pat. No. 5,380,690 discloses the single catalyst system comprising of Y-Zeolite and ZSM-5 to obtain yields of 17-20% propylene, 5-6% ethylene, and 12-14% other olefins at WHSV of 1-6 $hr^{-1}$.

U.S. Pat. No. 5,318,696 reported large pore zeolite and medium pore zeolite are employed to produce high octane gasoline and gaseous olefin. U.S. Pat. No. 7,375,256 discloses phosphorous and transition metal modified zeolites are utilized to produce ethylene 5-25%, propylene 21-26% and 5-14% other olefins with WHSV 1-200 $hr^{-1}$ and 550 to 750° C.

U.S. Pat. No. 5,326,465 (China Petro-Chemical Corporation) claims a catalytic cracking process to produce LPG which is rich in propylene and butylenes and high-octane gasoline using three zeolitic active components namely, rare earth containing high silica pentasil zeolite, rare earth Y zeolite and high silica Y zeolite. These three components constitute 10-40 wt % of the catalyst and the remainder constitutes silica or silica-alumina binder. Feed may constitute straight run fractions and a maximum 30 wt % of coker gas oil, deasphalted oil or its mixtures. The patent further describes that 1 to 150 $hr^{-1}$ WHSV is maintained to yield 27 to 35% LPG and 6-11% propylene and 5-17% other olefins.

U.S. Pat. No. 4,980,053 (Research Institute of Petroleum Processing, SINOPEC) describes a process for production of LPG rich in propylene and butylene from vacuum gas oil feedstock using pentasil and faujasite catalysts in a FCC process at a reaction temperature of 500-650° C., with a catalyst to oil ratio in the range of 2-12. The patent describes process to yield 15 wt % each of propylene and butylenes based on feed. WHSV of the process is 0.2 to 20 $hr^{-1}$.

U.S. Pat. No. 6,905,591 (Letszch, SWEC) is directed to a new catalytic reactor system as an improvement to above mentioned process, with two separate and distinct cracking zones with different radii to improve the selectivity of propene and butene as products in a FCC. The catalyst consists of commercially available rare earth exchanged zeolite component and a matrix component.

U.S. Pat. No. 9,616,408 describes a cracking catalyst to produce 31.5% LPG and propylene selectivity of 49% in fluidized bed reactor with riser temperature of 530-600° C. The patent describes a process employing a mixture or composite catalyst comprising ultrastable Y zeolite, shape selective pentasil zeolite, and a residue up gradation cracking component.

U.S. Pat. No. 5,846,402 discloses a process of selective catalytic cracking to produce 40-65 wt % of LPG containing at least 40 wt % of light olefins in a fluidized bed reactor operating with a catalyst to oil ratio of 15-25, WHSV of 40-120 $hr^{-1}$ riser temperature of 530-600° C. The patent describes a process employing a mixture or composite catalyst comprising ultra-stable Y zeolite containing rare earth components, shape selective pentasil zeolite, and a bottom cracking component.

All the above FCC processes reported in the existing literature describe that the catalyst composition enhances olefin and LPG at weight hour space velocity (WHSV) of 2 to 140 $hr^{-1}$ and higher operating temperature of 530 to 750° C.

The major limitations with existing catalyst composition are that the olefins can be enhanced to a certain limit and these olefin yields are obtained at a cost of high value gasoline and distillates yields, as well. Most of the processes operate at low WHSV of below 100 $hr^{-1}$ and riser out let temperature above 550° C.

Therefore, there is need for the catalysts employed for FCC operations to be robust towards high temperature regeneration, steam stripping under the dynamic conditions of the FCC operation. At the same time there is also a need for the catalysts that would exhibit high selectivity towards $C_3$ to $C_4$ olefins with minimal loss in yields of gasoline, naphtha and light cycle oil (LCO).

OBJECTIVES OF THE PRESENT INVENTION

The main object of the present invention is to provide a catalyst composition for enhancing yields of light olefins, like, propylene, isobutylene, c-2/t-2 butene. Further object of the invention is to provide a catalyst composition to arrest the losses of gasoline, heavy naphtha and light cycle oil (LCO). It is also an object of the present invention to provide a catalyst composition that enhances light olefin selectivity and at the same time also arrest the losses of gasoline, heavy naphtha and light cycle oil (LCO) in fluid catalytic cracking (FCC) process.

Another object of the invention, in particular, relates to a catalyst possessing required Attrition Index (AI), Average Bulk Density (ABD) and particle size distribution for smooth circulation of catalyst in FCC Unit with minimized catalyst loss.

Still another object of the invention is to provide catalyst composition which is capable of operating at low severity of catalyst/oil ratio of 6.

Yet another object of the invention is to provide a catalyst composition for enhancing selectivity of propylene in LPG.

SUMMARY OF THE INVENTION

The present invention provides a catalyst composition comprising: 10-25 wt % rare earth exchanged USY zeolite (REUSY); 5-20 wt % stabilized pentasil zeolite; 2-8 wt % phosphorous compound; 20-45 wt % clay; 5-25 wt % silica; 10-35 wt % alumina; and 0.5 to 3 wt % mixed metal oxide selected from a group consisting of at least one of and the wt. % being based on total weight of the catalyst.

In another feature, the present invention provides a composite catalyst composition comprising: 10-25 wt % rare earth exchanged USY zeolite (REUSY); 5-20 wt % stabilized pentasil zeolite; 2-8 wt % phosphorous compound; 20-45 wt % clay; 5-25 wt % silica; 10-35 wt % alumina; and 0.5 to 3 wt % mixed metal oxide selected from a group consisting of at least one of Group XI and XIII metals, and the wt. % being based on total weight of the catalyst. The said composite catalyst composition has an olefin selectivity, with minimal loss in yields of gasoline, naphtha and light cycle oil (LCO).

In addition, the present invention provides a process for preparing a composite form of the catalyst composition of the present invention for light olefin selective catalytic cracking of heavy oils in petroleum processing industry. The process comprises the steps of:
  (a) preparing a slurry of clay, alumina and phosphorous compound;
  (b) dispersing pentasil zeolite in the clay-alumina-phosphate slurry obtained in step (a) to obtain another slurry;
  (c) milling, spray drying, and calcining the slurry obtained in step b) to obtain a zeolite-clay-phosphate powder;
  (d) preparing a binder comprising of at least one of alumina and polysilicate;
  (e) sequentially dispersing the zeolite-clay-phosphate powder, mixed metal oxide selected from a group consisting of at least one of Group XI and XIII metals, REUSY zeolite, and silica into the binder to obtain a precursor slurry;
  (f) milling and spray drying the precursor slurry to obtain a spray dried product; and
  (g) calcining the spray dried product to obtain composite form of the catalyst composition.

In another feature, the present invention provides a process for preparing a composite catalyst composition for light olefin selective catalytic cracking of heavy oils in petroleum processing industry. The said process comprises:
  (a) preparing REUSY zeolite;
  (b) preparing a binder comprising of at least one of alumina and polysilicate;
  (c) preparing a spinel of mixed metal oxides selected from a group consisting of at least one of Group XI and XIII metals;
  (d) preparing stabilized pentasil zeolite;
  (e) sequentially dispersing clay, the REUSY zeolite, the stabilized pentasil zeolite, and the spinel in the binder to obtain a precursor slurry;
  (f) milling and spray drying the precursor slurry to obtain a spray dried product; and
  (g) calcining the spray dried product to obtain composite catalyst composition.

DETAILED DESCRIPTION OF THE INVENTION

While the invention is susceptible to various modifications and/or alternative processes and/or compositions, specific embodiment thereof has been shown by way of example in tables and will be described in detail below. It should be understood, however that it is not intended to limit the invention to the particular processes and/or compositions disclosed, but on the contrary, the invention is to cover all modifications, equivalents, and alternatives falling within the spirit and the scope of the invention as defined by the appended claims.

The tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particular and all details set forth herein are used in the context of some embodiments and therefore should not be necessarily taken as limiting factors to the attached claims. The attached claims and their legal equivalents can be realized in the context of embodiments other than the ones used as illustrative examples in the description below.

Accordingly, the present invention provides a Fluid Catalytic Cracking (FCC) catalyst composition comprising REUSY, pentasil zeolite with a stabilizer, silica, alumina, clay and spinel. The catalyst composition of the present invention possesses enhanced catalytic activity and selectivity towards production of light end olefins in total yield of slabs. It may be known to those involved in preparation and performance evaluation of FCC catalysts along with pentasil zeolite, that every enhancement in yield of light end is associated with loss in yield of high value gasoline, heavy naphtha and LCO. Limitations encountered in conventional FCC catalysts and additive system is being addressed in catalyst composition described in the present invention.

According to a preferred feature, the present invention provides an olefin selective catalyst composition comprising: 10-25 wt % rare earth exchanged USY zeolite (REUSY); 5-20 wt % stabilized pentasil zeolite; 2-8 wt % phosphorous compound; 20-45 wt % clay; 5-25 wt % silica; 10-35 wt % alumina; and 0.5 to 3 wt % mixed metal oxide selected from a group consisting of at least one of Group XI and XIII metals, and the wt. % being based on total weight of the catalyst.

According to another preferred feature, the present invention provides a process for preparing a composite catalyst composition for selective catalytic cracking of heavy oils in petroleum processing industry, wherein the process comprises:
- (a) preparing a slurry of clay, alumina and phosphorous compound;
- (b) dispersing pentasil zeolite in the clay-alumina-phosphate slurry obtained in step (a) to obtain another slurry;
- (c) milling, spray drying, and calcining the slurry obtained in step (b) to obtain a zeolite-clay-phosphate powder;
- (d) preparing a binder comprising of at least one of alumina and polysilicate;
- (e) sequentially dispersing the zeolite-clay-phosphate powder, mixed metal oxide selected from a group consisting of at least one of Group XI and XIII metals, REUSY zeolite, and silica into the binder to obtain a precursor slurry;
- (f) milling and spray drying the precursor slurry to obtain a spray dried product; and
- (g) calcining the spray dried product to obtain composite catalyst composition.

According to another feature of the present invention, the process for preparing olefin selective catalyst composition comprises the following sequence of steps:
- (a) preparing a rare earth exchanged USY zeolite;
- (b) preparing binder, selected from alumina and polysilicate;
- (c) preparing spinel;
- (d) preparing stabilized pentasil zeolite;
- (e) sequentially dispersing clay, REUSY zeolite, stabilized pentasil zeolite and spinel in silica-alumina binder;
- (f) passing the precursor slurry through colloid mill to ensure homogenization of all the components of catalyst;
- (g) spray drying the slurry of step (f); and
- (h) calcining the spray dried product of step (g) and cooling to room temperature to produce composite catalyst composition.

According to another embodiment, the present invention provides a catalytic cracking process for selective conversion of heavy hydrocarbons to light olefins, wherein the process comprises of contacting the heavy hydrocarbons with a light olefin selective composite catalyst of the present invention at lower reaction temperature of around 510 to 530° C. In a preferred feature, the said process is carried out at around 529° C. The composite catalyst enhances production of total olefin by about 1-2 wt %, propylene selectivity by about 1-3%, gasoline yield by about 1-3 wt %, and diesel yield by about 1-2 wt %. In a preferred feature, the composite catalyst of the present invention enhances production of total olefin by about 1.5 wt %, propylene selectivity by about 2%, gasoline yield by about 2.5 wt %, and diesel yield by about 1.6 wt %.

According to a feature of the present invention, the clay is selected with diluents and fillers to have minimum impurities such as sodium, $Fe_2O_3$, $TiO_2$, MgO, and quartz.

According to a feature of the present invention, the composite catalyst composition of the present invention is in the form of, but not limited to, at least one of pellet, extrude, tablet, or microsphere.

According to an aspect of the present invention, the catalyst composition is suitable for at least one of fixed bed or fluid bed catalytic cracking operation.

According to an aspect of the present invention, the REUSY is prepared by exchanging USY zeolite with salts of rare earth compounds. The salts are selected from at least one of hydroxides, chlorides, nitrates, sulphates, oxalates, carbonates, acetates, formates, and hydrates but free from sodium. In addition, the REUSY comprises of 0.1 to 5 wt % of rare earth oxide.

According to another aspect of the present invention, the REUSY is prepared preferably by exchanging USY zeolite with salts of Lanthanum rich compound.

According to yet another feature of the present invention, the silica is selected from at least one of sodium and ammonium stabilized colloidal silica with silica content varying in the range of 20-50 wt %. The alumina is selected from a group consisting of pseudoboehmite, boehmite, aluminum trihydrate, and gamma.

According to another feature of the present invention, the silica and alumina are taken in judicious weight, so that taken quantity is just enough to bind REUSY, clay, and spinel. According to another feature of the present invention, the pentasil zeolite is selected from a group consisting of ZSM-5, ZSM-11, mordenite, and beta. In addition, the phosphorous compound is sourced from a group consisting of at least one of mono-ammonium phosphate, di-ammonium phosphate, and phosphoric acid. The clay is selected from a group consisting of at least one of bentonite, attapulgite, and kaolinite.

According to yet another feature of the present invention, the mixed metal oxide may be selected from a group consisting of at least one of Group X, XI, XII, XIII metals. Preferably, the mixed metal oxide is selected from Groups XI and XIII metals.

According to another feature of the present invention, the mixed metal oxide comprises of metal selected from at least one of copper, nickel, zinc, aluminium, and mixtures thereof. More preferably, the mixed metal oxides comprises of copper and aluminium metals. In a preferred feature, the mixed metal oxide is copper aluminate.

According to an aspect of the present invention, the mixed metal oxide in the catalyst composition is a spinel. In a preferred feature, the spinel is a copper aluminate spinel.

A typical cracking process involves conversion of heavy hydrocarbons to desired olefins, especially light olefins in the presence of heterogeneous catalysts with large surface area and porosity. Metal oxides with solid supports, such as copper oxides are widely used as catalysts. However, the copper oxides are inherently crystalline in form of large crystals due to their cubic structure. This leads to lower dispersion of the copper oxide particles in catalysts and affects thermal and mechanical properties of the catalyst.

Therefore, the present invention utilizes copper aluminate spinel in the catalyst composition. The copper aluminate spinel in the catalyst composition enables effective exploitation of catalytic functionality of the copper aluminate spinel to control reaction network during cracking process, which further enhances yields of high value hydrocarbons in FCC.

Without being bound by the theory, the inventors of the present invention believe that the effective conversion of the heavy hydrocarbons to the desired olefins is attributed to the structural features of copper aluminate. The spinel structure of the copper aluminate enables effective dispersion of the active components of copper aluminate in the catalyst, thereby improving the overall surface area, porosity, and thermal/mechanical stability of the catalyst.

According to an aspect of the present invention, the spinel, preferably copper aluminate spinel, present in the catalyst composition helps to reduce the formation of coke with selectivity of propylene in LPG of around 40 wt % with minimum loss in Gasoline (around 21.6%), and distillate yield (around 25%) while cracking the heavier hydrocarbon molecules.

According to another aspect, the present invention provides the catalyst composition with improved light olefin selectivity in the range of 35-40%.

According to yet another aspect of the present invention, fine dispersion of the spinel at low concentrations in the range of 0.5 to 3 wt % in conjunction with other components such as alumina matrix, ZSM-5 zeolite and Re-USY results in the high distillate and gasoline yield.

According to a feature of the present invention, the spinel is prepared by co-precipitation method. More specifically, the spinel is prepared by dispersing Group XI metal oxide and alumina in demineralized (DM) water followed by spray drying and calcination.

According to yet another feature of the present invention, the spinel is preferably prepared by dispersing metal oxides of copper compound, preferably copper hexanitrate, and alumina in DM water followed by spray drying and calcination.

According an embodiment the catalyst may be a composite of FCC catalyst, ZSM-5 additive, residue up-gradation additive and a spinel additive with desired particle size in the range of 80-90 micron, ABD in the range of 0.78 to 0.85 g/cc, attrition index (AI) of around 3%. A preferred catalyst composition of the present invention comprises about 15 wt % rare earth exchanged USY zeolite (REUSY), about 12 wt % stabilized pentasil zeolite, about 4.2 wt % phosphorous compound, about 37.8 wt % clay, about 11.5 wt % silica, about 18.05 wt % alumina, and about 1.5 wt % copper aluminate spinel.

According to another feature, the present invention provides the catalyst composition, comprising introducing the REUSY, stabilized pentasil zeolite, silica, and clay along with the spinel to an alumina binder and shaping the mixture obtained to microspheroidal form and further calcination to harden the microspheres suitable for fluidization and circulation.

Further, according to yet another feature, the present invention provides a process for the preparation of catalyst composition for catalytic cracking of hydrocarbons to provide higher conversion, higher yield of light end olefins, naphtha yield and lower bottoms.

According to yet another feature, the present invention provides a composite catalyst composition, which enhances light olefin yield in an amount of about 1.5%, selectivity of propylene in LPG in the range of 35-40%, retention of gasoline in the range of 19-22 wt % and retention of diesel in the range of 23-26 wt %.

According to an aspect, the present invention provides a composite catalyst composition that enables improved selective catalytic cracking of heavy oils in petroleum processing industry at cat/oil ratio of about 6 and riser outlet temperature of about 529° C.

EXAMPLES

The present invention is exemplified by following non-limiting examples:

Example-1: Preparation of RE-USY

This example illustrates the process for preparation of rare earth exchange Y zeolite. Hydrothermally stable, large crystallite sized USY zeolite was taken as the starting zeolite. REUSY was prepared as per Example 2 of U.S. Pat. No. 6,528,447B1, which is incorporated herein by reference, having surface area 720 m$^2$/g, unit cell size (UCS) 24.55 A, rare earth content 4 wt % by rare earth exchange with 1% rare earth chloride solution.

Example-2: Preparation of FCC Catalyst

FCC catalyst was prepared as per example 3 of U.S. Pat. No. 6,528,447B1, which is incorporated herein by reference, employing rare earth exchanged USY of example 1, ammonium polysilicate, pseudo-boehmite alumina and kaolin clay. The final catalyst product had following composition: REUSY 25 wt %, alumina 30 wt %, kaolin clay 40 wt % and silica 5 wt % having properties, surface area 240 m$^2$/g, ABD 0.76 g/cc, AI<6, average particle size 80 micron.

Example-3: Preparation of Residue Up Gradation (RUA) Catalyst

Residue up-gradation catalyst was prepared as per example 3 of co-pending U.S. Ser. No. 14/857,449, which is incorporated herein by reference, free of any zeolite. Final catalyst possesses ABD of 0.8 g/cc, surface area of 50 m$^2$/g, average particle size 82 micron.

Example-4: Preparation of ZSM-5 Additive 98.63 gm of Pural SB grade alumina (having loss on ignition of 23.96 wt %) was made into a slurry with 425 gm of DM water. The slurry was peptised with 21.52 gm of formic acid (85% concentration). 750 gm of ZSM-5 zeolite (loss on ignition 12.12 wt %) having silica to alumina molar ratio of 30 was made into a slurry with 862 gm of 10% ammonical solution followed by addition of 27.7 g phosphoric acid (85%) to produce a zeolite slurry having pH of 7.5. 635 gm of kaolin clay (having loss on ignition 14.91 wt %) was made into a slurry with 685 gm DM water and kept under vigorous stirring while 191.53 gm of ortho-phosphoric acid (concentration 85 wt %) was added. To clay-phosphate slurry earlier prepared alumina sol and zeolite slurry were added one after another under vigorous stirring. Final slurry having pH of 2.53 was spray dried similar to slurry of example 1 and the product was processed further. Spray dried product showed ABD of 0.79 with attrition index of 2.2. This catalyst has shown LPG yield of 18.2 wt % with a conversion of 60.2%. Final catalyst had surface area 155 m$^2$/g, ABD 0.79 g/cc, average particle size 85 micron.

Example-5: Preparation of Copper Aluminate Spinel

Copper aluminate spinel was prepared by co-precipitation method. Copper nitrate hexahydrate 242 g and aluminium sulphate 630 g was dissolved in 5000 ml DM water. 320 g Sodium hydroxide was dissolved in 1000 g DM water. Sodium hydroxide solution was sequentially added into acidic solution till pH of the reaction mixture reach to 10.5. The reaction was conducted at 35-45° C. under constant stirring condition. After an hour, the precipitate was filtered, washed with hot DM water five times to remove sodium salt.

The final washed material was dried at 120° C. for 10 hours, and then calcined at 850° C. for 2 hour.

Example-6: Preparation of Composite Catalyst (Present Invention)

This example illustrates a process of preparing composite catalyst of present invention as an alternate composition. 140 gm of ZSM-5 zeolite, silica to alumina ratio 29 was dispersed in clay-alumina-phosphate slurry prepared by mixing 110.55 gm of clay and 33.37 gm of PSB alumina in 502 gm di-ammonium hydrogen phosphate solution (72.25 DAHP in 430 gm of DM water). Final slurry was ball milled and spray dried and the resulting powder after calcination at 510° C., was pulverized to particle size below 5 microns. 142.5 gm PSB alumina was dispersed in 1300 gm of DM water and the slurry was acidified with 42 gm of 85% formic acid. To the alumina gel, 237 gm of clay was added, followed by addition of 375 gm of pulverized stabilized ZSM-5-clay-phosphate powder prepared as above, 37.5 gm of milled spinel (prepared by dispersing 9.1 gm $Cu(OH)_2$ and 30 gm of alumina in 47 gm of DM water followed by spray drying and calcination), added 125 gm of REUSY powder prepared as per example-1. Finally, 125 gm of silica (as ammonium polysilicate) was added under stirring to obtain catalyst precursor slurry. Green catalyst of present invention was prepared by spray drying at outlet temperature 120° C., inlet 375° C. Spray dried product was calcined to 550° C. for one hr to yield final olefin maximization catalyst microspheres. The catalyst was steam deactivated at 810° C. for 5 hrs and performance evaluation was carried in a fluid bed MAT unit at cat:oil ratio 6.

The above weights are volatile free basis.

Example-7: Performance of Catalyst Comprising FCC Catalyst, RUA, ZSM-5 and Spinel This example illustrates performance of composite catalyst prepared as per example 2, 3, 4, and 5. In general, according to the present invention, the catalyst comprises FCC catalyst, RUA, ZSM-5, and spinel in a ratio of 60 to 70:1 to 10:20 to 30:1 to 10, respectively. For this specific example, the catalyst was prepared comprising FCC catalyst, RUA, ZSM-5, and spinel in the ratio of 60:5:30:5, respectively.

The composite catalyst was steam deactivated at 810° C. for 5 hrs and performance evaluation was carried in a fluid bed MAT unit at cat:oil ratio 6. The performance of the catalyst is given below in Table 2.

Example-8: Performance of Catalyst Comprising FCC Catalyst, RUA and ZSM-5

This example illustrates performance of composite catalyst comprising catalyst of example 2, 3 and 4. In general, according to the present invention, the catalyst comprises FCC catalyst, RUA and ZSM-5 in a ratio 60 to 70:1 to 10:20 to 30, respectively. For this specific example, the catalyst was prepared comprising FCC catalyst, RUA and ZSM-5 in the ratio of 65:5:30, respectively.

The composite catalyst was steam deactivated at 810° C. for 5 hrs and performance evaluation was carried in a fluidized bed MAT unit at cat:oil ratio 6. The performance of the catalyst is given in below Table 2.

Properties of feed where all the above additives prepared as per examples-3 to 7 are evaluated are given in below Table-1, and Physico-chemical properties of final catalyst and steam deactivated product is shown in Table-2:

TABLE 1

| | Feed properties | | |
|---|---|---|---|
| Sr. No. | Attributes | Unit | Value |
| 1 | Density @ 15° C. | g/cc | 0.89 |
| 2 | Distillation, D-1160 | | |
| 3 | IBP | ° C. | 250.0 |
| 4 | 5% | ° C. | 321.0 |
| 5 | 30% | ° C. | 397.0 |
| 6 | 50% | ° C. | 428.0 |
| 7 | 70% | ° C. | 459.0 |
| 8 | Sulphur | wt % | 0.4 |
| 9 | CCR | wt % | 0.2 |
| 10 | V | ppm | 1 |
| 11 | Ni | ppm | 1 |
| 12 | Na | ppm | 2 |

TABLE 2

| | Performance of catalyst of examples 6-7 | | | | |
|---|---|---|---|---|---|
| | Catalyst composition similar to describe in U.S. Pat. Nos. 5,846,402 FCC + BCA + ZSM-5 | Present Invention Catalyst of example 6 Single microsphere of Alumina, ZSM-5, Z-Y and Cu-aluminate | Physical mixture Catalyst of example 7 Physical mixture of FCC, RUA, ZSM-5 and Cu-aluminate | Catalyst of example 8 Physical mixture of FCC, RUA, ZSM-5 | Catalyst without RUA, ZSM-5 and copper aluminate |
| Cracking Temperature, *c. | 529.0 | 529.0 | 529.0 | 529.0 | 529.0 |
| Injection Time, sec | 30.0 | 30.0 | 30.0 | 30.0 | 30.0 |
| Catalyst strip Time, sec | 360 | 360 | 360 | 360 | 360 |
| Recovery, wt % | 99.1 | 95.6 | 98.2 | 98.7 | 98.7 |
| Catalyst-to-oil, wt/wt | 6.00 | 6.00 | 6.00 | 6.0 | 6.0 |

TABLE 2-continued

Performance of catalyst of examples 6-7

| | Catalyst composition similar to describe in U.S. Pat. Nos. 5,846,402 FCC + BCA + ZSM-5 | Present Invention Catalyst of example 6 Single microsphere of Alumina, ZSM-5, Z-Y and Cu-aluminate | Physical mixture Catalyst of example 7 Physical mixture of FCC, RUA, ZSM-5 and Cu-aluminate | Catalyst of example 8 Physical mixture of FCC, RUA, ZSM-5 | Catalyst without RUA, ZSM-5 and copper aluminate |
|---|---|---|---|---|---|
| Conv., wt % | 71.43 | 70.63 | 72.7 | 72.06 | |
| Yields, wt % | | | | | |
| Coke | 6.488 | 3.86 | 6.7 | 6.62 | 5.76 |
| Dry gas | 2.825 | 2.74 | 3.19 | 3.01 | 0.82 |
| Ethylene | 2.279 | 2.25 | 2.50 | 2.43 | 0.04 |
| Propane | 2.816 | 2.32 | 3.11 | 2.96 | 0.67 |
| propylene | 13.376 | 13.86 | 13.64 | 13.51 | 4.5 |
| n-Butane | 1.563 | 1.26 | 1.60 | 1.58 | 0.53 |
| Isobutene | 3.948 | 3.01 | 3.71 | 3.83 | 2.61 |
| C4 Olefins | 13.591 | 14.04 | 13.28 | 13.48 | 8.32 |
| 1-butene | 2.102 | 2.20 | 2.06 | 2.08 | 1.48 |
| Isobutylene | 5.581 | 5.79 | 5.54 | 5.56 | 3.02 |
| C-2 Butene | 2.496 | 2.56 | 2.44 | 2.47 | 1.61 |
| Total light olefin | 42.8 | 44.0 | 42.9 | 42.8 | 42.8 |
| t-2-Butene | 3.394 | 3.45 | 3.33 | 3.36 | 2.17 |
| Gasoline (C5 to 160° C.) | 19.118 | 21.60 | 18.76 | 18.94 | 35.0 |
| HN (160 to 216° C.) | 7.708 | 7.96 | 8.52 | 8.12 | 13.2 |
| LCO (216 to 370° C.) | 16.045 | 17.43 | 13.35 | 14.70 | 18.9 |
| Diesel (HN + LCO) | 23.753 | 25.39 | 21.87 | 22.81 | 32.1 |
| Bottoms | 12.522 | 11.93 | 13.97 | 13.25 | 10.0 |
| Total | 100.00 | 100.00 | 100.00 | 100.0 | |
| Propylene in LPG (%) | 37.898 | 40.19 | 38.5 | 38.2 | 27.0 |
| LPG | 35.295 | 34.48 | 35.44 | 35.3 | 16.6 |
| LPG/(Gasoline + Diesel) | 1.87 | 0.73 | 0.88 | 0.84 | 0.25 |

Performance Evaluation as Per Results Shown in Table-2

It is evident from the Table-2 that performance of the composite catalyst comprising copper aluminates spinel (as illustrated in example-6) enhances the total olefin by +1.2 wt % and propylene selectivity in LPG by 2% along with enhancing gasoline and diesel by 2.5 wt % and 1.6 wt %, respectively.

The superior performance is attributed to close proximity of the copper aluminate spinel with ZSM-5 in combination with the method of preparation and the synergistic effect of alumina, ZSM-5 zeolite and Re-USY in the composition. This in-turn results in the high distillate and gasoline yield.

The invention claimed is:

1. A composite catalyst composition, the composition comprising:
   about 10-25 wt % rare earth exchanged USY zeolite (REUSY);
   about 5-20 wt % pentasil zeolite;
   about 2-8 wt % phosphorous compound;
   about 20-45 wt % clay;
   about 5-25 wt % silica;
   about 10-35 wt % alumina; and
   about 0.5 to 3 wt % mixed metal oxide selected from a group consisting of at least one metal of Group 11 and one metal of Group 13, and the wt % being based on total weight of the catalyst composition.

2. The composition as claimed in claim 1, wherein the mixed metal oxide is a spinel.

3. The composition as claimed in claim 1, wherein the mixed metal oxide is selected from a group consisting of at least one of copper, aluminium, and mixtures thereof.

4. The composition as claimed in claim 1, wherein the pentasil zeolite is selected from a group consisting of ZSM-5 and ZSM-11.

5. The composition as claimed in claim 1, wherein the REUSY comprises of 0.1 to 5 wt % of rare earth.

6. The composition as claimed in claim 1, wherein the phosphorous compound is selected from a group consisting of at least one of mono-ammonium phosphate, di-ammonium phosphate, and phosphoric acid.

7. The composition as claimed in claim 1, wherein the clay is selected from a group consisting of at least one of bentonite, attapulgite, and kaolinite.

8. The composition as claimed in claim 1, wherein the silica is selected from at least one of sodium and ammonium stabilized colloidal silica with silica content varying in the range of 20-50 wt %.

9. The composition as claimed in claim 1, wherein the alumina is selected from a group consisting of pseudoboehmite, boehmite, aluminum trihydrate, and gamma.

10. The composition as claimed in claim 1, wherein the composite catalyst composition is in the form of at least one of pellet, extrude, tablet, and microsphere.

* * * * *